United States Patent [19]
Lippert et al.

[11] Patent Number: 5,250,811
[45] Date of Patent: Oct. 5, 1993

[54] METHOD FOR DETERMINING COMPOSITIONAL INFORMATION OF A MULTILAYER WEB

[75] Inventors: Joseph E. Lippert; Russell Jacobsmeyer, both of Rochester, N.Y.

[73] Assignee: Eastman Kodak Company

[21] Appl. No.: 812,247

[22] Filed: Dec. 20, 1991

[51] Int. Cl.$^5$ ................... G01N 21/25; G01N 21/31; G01N 21/35

[52] U.S. Cl. ................... 250/339; 250/340; 250/341; 250/359.1

[58] Field of Search ........... 250/339, 340, 341, 358.1, 250/359.1, 571; 356/73

[56] References Cited

U.S. PATENT DOCUMENTS

| | | | |
|---|---|---|---|
| 3,008,369 | 11/1961 | Zuk | 356/51 |
| 3,405,268 | 10/1968 | Brunton | 250/339 |
| 3,551,678 | 12/1970 | Mitchell | 250/341 |
| 3,641,349 | 2/1972 | Dahlin | 250/350 |
| 3,661,462 | 5/1972 | Natens | 356/51 |
| 3,675,019 | 7/1972 | Hill et al. | 250/350 |
| 3,793,524 | 2/1974 | Howarth | 250/339 |
| 4,006,358 | 2/1977 | Howarth | 250/339 |
| 4,097,743 | 6/1978 | Carlson | 250/339 |
| 4,243,882 | 1/1981 | Yasujima et al. | 250/339 |
| 4,289,964 | 9/1981 | Baker | 250/308 |
| 4,345,150 | 8/1982 | Tamura et al. | 250/339 |
| 4,429,225 | 1/1984 | Fumoto et al. | 250/353 |
| 4,510,389 | 4/1985 | Fumoto | 250/339 |
| 4,574,194 | 3/1986 | Coats et al. | 250/308 |
| 4,577,104 | 3/1986 | Sturm | 250/341 X |
| 4,602,160 | 7/1986 | Mactaggart | 250/341 |
| 4,718,026 | 1/1988 | Long et al. | 250/339 X |
| 4,786,817 | 11/1988 | Boissevain et al. | 250/571 |
| 4,840,706 | 6/1989 | Campbell | 162/198 |
| 4,879,471 | 11/1989 | Dahlquist | 250/359.1 |
| 4,885,709 | 12/1989 | Edgar et al. | 364/563 |
| 4,943,721 | 7/1990 | Vidrine, Jr. | 250/308 |
| 4,957,770 | 9/1990 | Howarth | 427/9 |
| 5,019,710 | 5/1991 | Wennerberg et al. | 250/341 |
| 5,073,712 | 12/1991 | Hellstrom | 250/341 X |

FOREIGN PATENT DOCUMENTS 1326904 7/1987 U.S.S.R. ................ 250/341

OTHER PUBLICATIONS

Huizinga et al. "Application of Infrared Spectroscopy to On-Line Monitoring of Thin Coatings", Abstracts of the 1986 Conference of the Federation of Analytical Chemistry and Spectroscopy Societies, 1986.

Huizinga, "Comparison of Near-IR and Mid-IR Spectroscopic Techniques Used for On-Line Quality Control of Moving Webs", Abstracts of the 1991 Pittsburg Conference of Analytical Chemistry and Applied Spectroscopy, 1991.

Fukada et al., "FTIR Study on the Nature of Water Sorbed in Poly(ethylene terephthalate) Film", Chemtracts-Macromolecular Chemistry 2:188-190 (1991).

Willey, "Fourier Transform Infrared Spectrophotometer for Transmittance and Diffuse Reflectance Measurements", Applied Spectroscopy, vol. 30, No. 6, 1976, pp. 593-601.

*Primary Examiner*—Constantine Hannaher
*Assistant Examiner*—Edward J. Glick
*Attorney, Agent, or Firm*—Foley & Lardner

[57] ABSTRACT

A method for obtaining quantitative compositional information from a multilayer web containing a highly light-scattering component. The compositional information is obtained by measuring and analyzing the transmitted or diffusely reflected infrared spectrum. The method allows for separately determining the moisture content of hydrophobic (non-hydrogen bonding) layers and hydrophilic (hydrogen bonding) layers of multilayer webs. The separate measurements of moisture content can be made simultaneously in moving webs having both types of layers present. The method is used to determine further compositional information such as the thickness of the individual support and gelatin containing layers, plasticizer content, retained solvents content, and the presence of other components in webs, especially photographic webs.

13 Claims, 10 Drawing Sheets

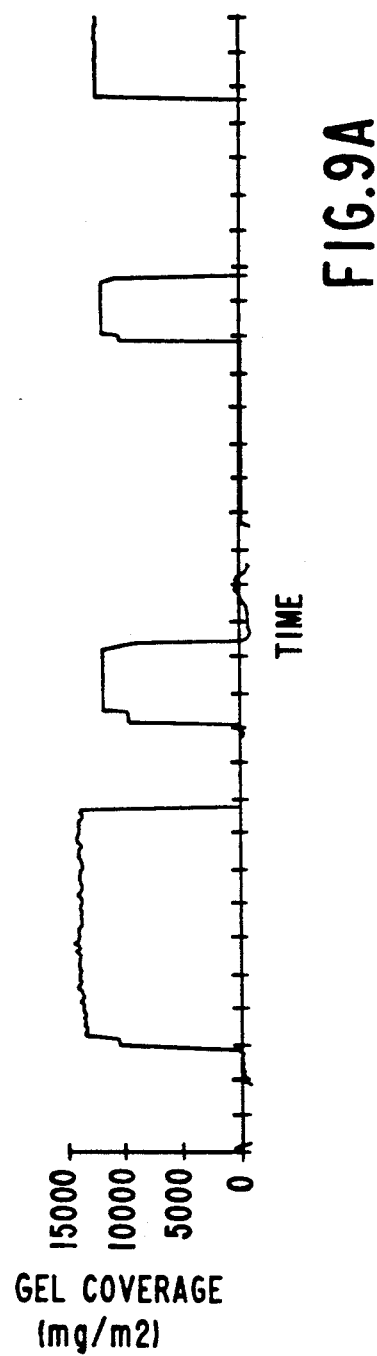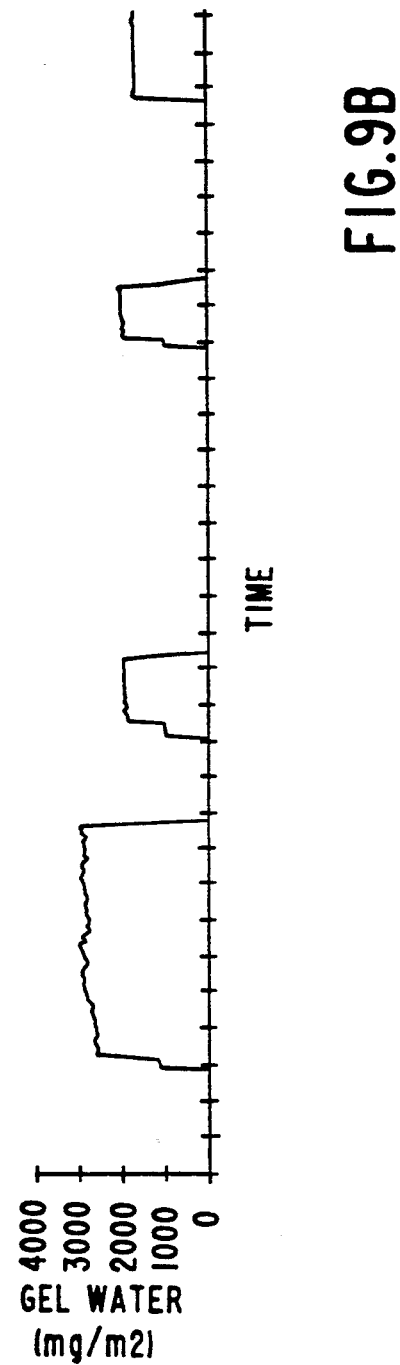

METHOD FOR DETERMINING COMPOSITIONAL INFORMATION OF A MULTILAYER WEB

BACKGROUND OF THE INVENTION

The present invention relates generally to a method for deriving compositional information. More specifically the invention relates to a method for determining the separate moisture contents and other compositional information for layered webs containing hydrogen bonding or hydrophilic and/or non-hydrogen bonding or hydrophobic layers, including but not restricted to photographic film or paper or their precursor support webs.

The measurement of moisture in moving webs, particularly in paper, has been the subject of a number of patents. See U.S. Pat. Nos. 3,405,268, Brunton; 3,551,678, Mitchell; 3,641,349, Dahlin; 3,675,019, Hill; 3,793,524, Howarth; 4,006,358, Howarth; 4,097,743, Carlson; 4,345,150, Tamura; 4,840,706, Campbell. These patents disclose methods and apparatuses that measure the intensity of transmitted or reflected light through a series of optical filters that transmit selectively in the near-infrared (NIR) region of the spectrum (0.8 to 2.5 micrometers). One filter passes light at a wavelength which is water absorbing, generally specified as 1.94 micrometers, while a second filter passes light at a wavelength that water does not absorb, typically 1.8 micrometers. Some patents further disclose use of an additional filter at a wavelength where the web (e.g., cellulose) absorbs light, and even a fourth filter at a wavelength where the web does not absorb light.

Attempts to use such a device to measure the moisture content of photographic film after drying have produced very noisy results and in general a poor correlation with other moisture measurement techniques. During research associated with the present invention, examination of the transmission infrared spectrum of photographic film webs revealed that the very small features associated with absorption by water in the NIR are superimposed on a very large background of light attenuation that is associated with light scattering by the silver halide particles in the emulsion layers of the film. This background attenuation increases at shorter wavelengths and is generally not reproducible in either absolute amount or in the amount of change with wavelength between films.

Background attenuation has two effects. First, the wavelengths at which water and web do not absorb have a large underlying absorbance (due to light scattering) relative to the additional absorbance of water or web at their respective measurement wavelengths. The absorbance due to light scattering results in a very small moisture signal relative to a very large, noisy background and thus a very noisy and unsatisfactory measurement. Second, the fact that the baseline changes with wavelength and that the change is different from coating to coating is not compensated for when a single reference wavelength is used for each measurement wavelength.

A further disadvantage of available NIR filter-type moisture measurement systems is that a single wavelength is used to obtain the measure of moisture. If water in the different layers of a web had exactly identical absorption properties as a function of wavelength, then the measurement outlined above would provide a signal proportional to the total amount of moisture in the entire web if the measurement were made with transmitted light. If the measurement is made with reflected or diffusely scattered light, the measurement signal would be proportional to the total amount of water in that fraction of the cross section of the web that light penetrated to before it was reflected or scattered. The prior art apparently assumes that water in different layers of a web has identical absorption properties as a function of wavelength.

During research associated with the present invention, it has been discovered that water contained in different chemical environments has different spectra in both the mid-infrared (2.5–14 micrometers) and the near infrared (0.8–2.5 micrometers) wavelength regions. These differing spectra indicate that the amount of light absorbed by a given amount of water at a given wavelength will depend on the environment in which the water is contained, and in particular whether the water is hydrogen bonded or not hydrogen bonded to the molecules in a given environment.

For photographic film and paper products the wavelength 1.94 micrometers is absorbed to a much greater extent by non-hydrogen bonded water in a hydrophobic environment (as in synthetic polymer supports such as cellulose acetate or polyethylene terephthalate, or in paper) than by the water that is hydrogen bonded as in the gelatin in the emulsion layers of the photographic product. These differing absorptions mean that the signal measured by simple NIR filter moisture devices is not a simple measurement of the total amount or fraction of water in the entire web. At the same time the desirable result of separate measures of water in support and of water in the emulsion layers cannot be obtained either.

A further disadvantage of filter-type infrared instruments for web measurement is that they require at least one measurement wavelength filter for each composition component measured (more typically an additional reference wavelength filter per component as well). In many web coating processes there is a large variation in the components of the support and coated layers so that it becomes very difficult to provide a filter-based infrared instrument with enough flexibility to measure the components of these varied coating processes because the number of filters required becomes too large to provide rapid feedback.

Hence, there is a need for a much more flexible system that would involve obtaining the entire spectrum (light intensity as a function of wavelength) in all cases and providing an analysis system that can recognize the product variations and select appropriate wavelengths to analyze the specific product being coated.

Another disadvantage of present measuring methods involves webs that are not completely dry. When taking the background spectrum through open air, present methods generally require that the moving web be stopped and removed. Taking a background spectrum over a stopped web does not accurately portray the components of the open air over a moving web.

In summary, the disadvantages of present filter-based NIR measurements for moving webs include (1) they provide noisy and inaccurate measurements in the case of webs that contain highly scattering media, (2) they provide inadequate selectivity to measure water in different chemical environments, (3) they provide inadequate flexibility for situations in which the components of the web change greatly in batch coating processes, and (4) they fail to account for open air composition over moving non-dry webs.

Vidrine (U.S. Pat. No. 4,943,721) discloses the combined use of an FTIR (Fourier transform infrared) thickness gauge and a beta gauge wherein the FTIR gauge is used to coarsely set parameters that improve the beta gauge thickness measurement. Huizinga and others disclose the use of mid-infrared FTIR measurements for monitoring of thin film coatings. See "Application of Infrared Spectroscopy to On-Line Monitoring of Thin Coatings"; J. S. Huizinga, E. Rudin and N. G. Constantine; presented at the Annual Meeting of the Federation of Analytical Chemistry and Spectroscopy Societies, St. Louis, 1986; and "Comparison of Near-IR and Mid-IR Spectroscopic Techniques Used for On-Line Quality Control of Moving Webs"; J. S. Huizinga; presented at the Pittsburgh Conference, Chicago, 1991. U.S. Pat. No. 4,243,882 discloses a method for measuring the thicknesses of film layers by using infrared rays. The '882 patent method uses several sample wavelengths and a reference wavelength.

SUMMARY OF THE INVENTION

It is an object of this invention to provide a method for measuring moisture contents of a multilayer web whereby separate moisture contents measurements are made for layers containing hydrogen bonding gelatin and layers containing non-hydrogen bonding support material.

It is another object of this invention to provide a method for more accurately measuring moisture contents of a multilayer web by increasing the moisture signal and decreasing the background noise.

It is a further object of this invention to provide a method for determining compositional information of a multilayer web that is adaptable for use with multiple film types and multiple support types.

It is a still further object of this invention to provide a method for determining compositional information of a multilayer web whereby each data collection step includes information on all components.

It is yet another object of this invention to provide a method for determining compositional information of a multilayer web by use of a Fourier transform infrared (FTIR) spectrometer alone.

A further object of this invention is to provide a method for determining compositional information of a multilayer web that is moving at speeds up to 600 meters/minute.

To accomplish these and other objects of the invention, a method for determining the compositional information of a multilayer web includes the steps of determining at least one set of coefficients from specimens of multilayer webs having known compositional information; projecting a broad spectrum of infrared rays onto a sample web to obtain a sample single beam spectrum of the web; projecting a broad spectrum of infrared rays through open air off the sample web to obtain a single beam background spectrum; calculating a sample spectrum from the single beam background and sample single beam spectra, the sample spectrum being corrected for light scattering effects; integrating the corrected sample spectrum over selected wavenumber ranges to define sample integrated values; comparing the sample integrated values to standard integrated values for different support types to determine the type of support in the sample; and combining the sample integrated values with the coefficients to solve at least one equation for the values of the items of compositional information to be determined.

Other objects and advantages of the invention will become apparent from the following detailed description of the preferred embodiments as described in conjunction with the accompanying drawings. The accompanying drawings are hereby expressly made a part of the specification.

BRIEF DESCRIPTION OF THE DRAWINGS

FIGS. 9A-D show results of the method applied to a moving web.

DETAILED DESCRIPTION OF THE PREFERRED EMBODIMENTS

Figure 1:
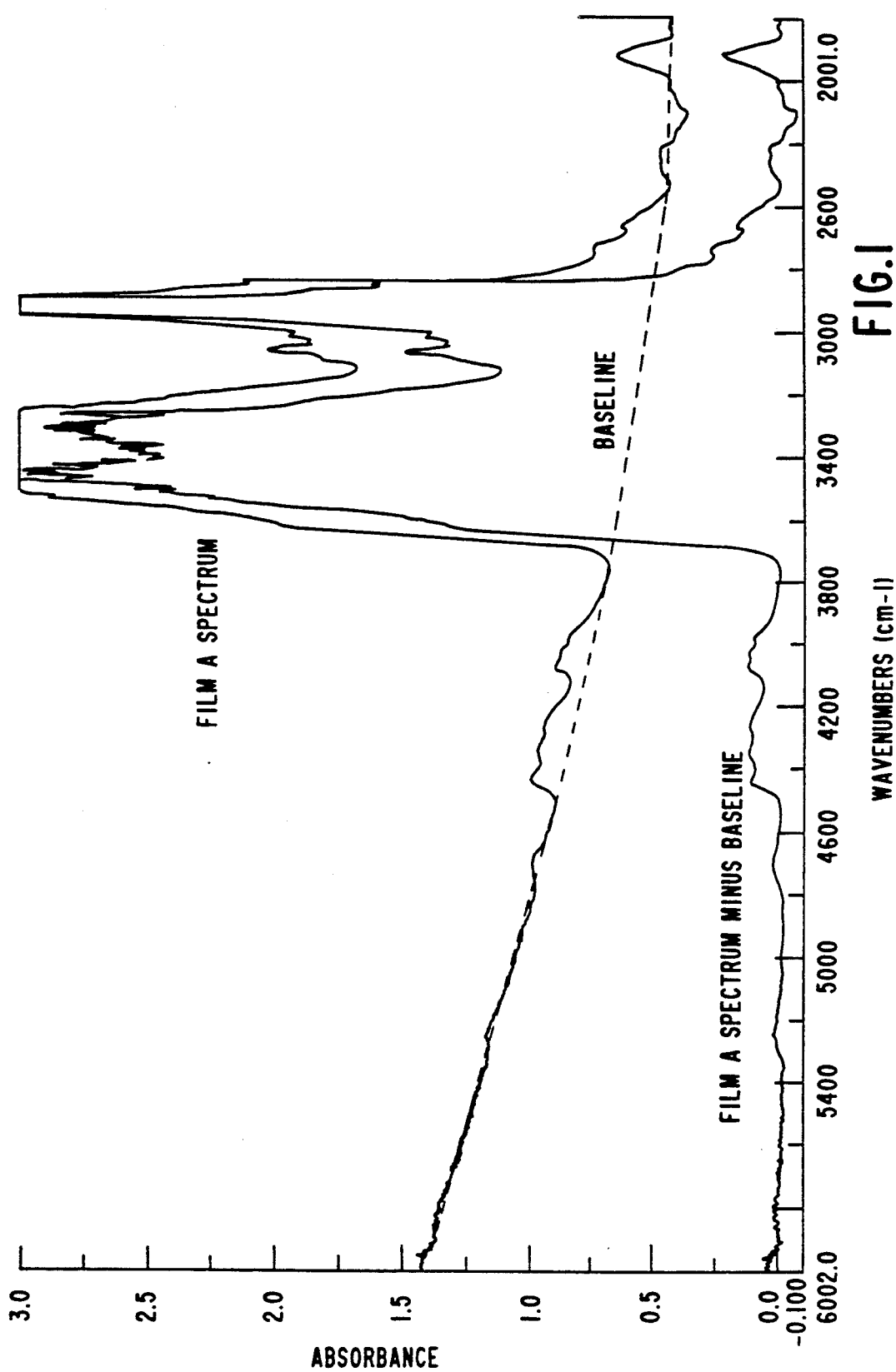
FIG. 1 shows a sample absorbance spectrum, baseline absorbance spectrum, and corrected sample absorbance spectrum for film A.

It has been discovered that, for webs that are thin enough that the absorbance in a measurement region is less than 3.5 absorbance units greater than the baseline absorbance and which are irregular enough that interference fringes due to reflections from multiple interfaces are not observed, mid-infrared FTIR measurements can have substantial advantages over NIR measurements and no problems or increases in noise are observed for moving versus static coatings. These advantages are particularly apparent in the case of photographic film where the emulsion layers that contain silver halide induce substantial diffuse scattering and therefore no interference fringes are observed.

A common practice in spectroscopic techniques is to use the inverse of wavelength, that is, wavenumber (1/cm), in the mid-infrared region of the spectrum, but in the near-infrared region to use wavelength in micrometers. That practice is followed in this description.

Prior to determining the compositional information of a web, referred to as the "sample" web, a set of absorbance coefficients or calibration factors is required. The process for obtaining the absorption coefficients is described in detail after the measurement method is discussed.

The next three steps in this invention involve obtaining a full infrared absorbance (or diffuse reflectance) spectrum of the sample web. Obtaining an absorbance spectrum consists of obtaining a "single beam" background spectrum through an open path that has the same through-space distance and the same humidity as does the path that includes the web. This background spectrum is a signal from the detector, usually referred to as $I_o$, that contains the variations in intensity of the source versus wavenumber, the variations in throughput of the spectrometer versus wavenumber, the variations in sensitivity of the detector versus wavenumber and the attenuations of the signal associated with absorbing materials in the through-space infrared beam path, particularly water vapor. This background spectrum should be taken at a detector gain that the instrument manufacturer specifies as optimum for the obtained signal.

Prior art methods typically obtain the single beam background spectrum by stopping and removing the moving web. It is more accurate to take the single beam background spectrum in an open air area immediately adjacent to the moving web, while the web is moving at process speed. In the case of a moist moving web, the air surrounding the web through which the sample spectrum is taken contains a certain percentage of the moist component in vapor form. When the moving web is stopped, the percentage of the moist component in vapor form in the surrounding air decreases. If the background spectrum is taken with the web stopped, the background spectrum will not account for the vaporized component which is present when the web is moving. Therefore, the background spectrum will not be an accurate measurement of the actual open air condition surrounding a moving web. The inaccuracy in the background spectrum will persist throughout the method and result in inaccurate compositional measurements.

To avoid the inaccuracy in the background spectrum, the method of the invention takes a background spectrum in the area immediately adjacent to the moving web while the web is moving at process speed. A background spectrum can be taken with the web in place and moving by routing the infrared beam via optical fibers to a second head of a single main detector. The background spectrum taken in this way more accurately represents the composition of the open air surrounding the moving web. A "sample single beam" spectrum is taken through the web, but with the gain reset so that it is optimum for that obtained signal. This spectrum is usually referred to as $I_s$, the "sample single beam spectrum." The "transmittance" spectrum is then generated by dividing $I_s$ by $I_o$ at all wavenumbers. Finally, the absorbance spectrum is calculated by taking the negative logarithm of the transmittance spectrum. These steps arrive at a spectrum of signal, A (absorbance) versus wavenumber where the signal is known to be proportional to the sums of the products of the concentration of each component ($c_i$) times the absorbance coefficient of that component at each wavenumber ($a_i$) times the thickness of the sample, according to Beer's Law.

$$A = -\log(I_s/I_o) = \sum_{\text{components, } i} [a_i \times (c_i \times 1)]$$

For the case of a pure component the product of concentration times thickness reduces simply to the thickness of that component and hence in that case Beer's Law provides a measure of the coated thickness of a layer, as, for example, the gel laydown or moisture content in mg/m$^2$ or the support thickness in micrometers, provided the absorbance coefficient is obtained in correct units of absorbance per mg/m$^2$ or absorbance per micrometer, respectively. It should be clear from the above that an analysis of concentration can be made directly from the sample single beam spectrum or transmittance spectrum provided the steps above are used to obtain equations relating these to concentration and thickness. Such methods are, of course, completely equivalent to obtaining the absorbance spectrum as described here. A completely analogous set of steps arrives at a diffuse reflection spectrum that is proportional to the product of turbidity times path length.

If diffuse reflection rather the absorption is measured, the single beam background spectrum is obtained by reflecting, in a diffuse manner, the projected beam off a pure white reflector to the collection detector. The pure white reflector is non-absorbing in the wavelength region of interest. The sample single beam spectrum is then measured by reflecting the projected beam from the web and collecting the diffusely scattered infrared rays. The diffuse reflectance spectrum (R) is then calculated as the ratio of the diffuse reflectance from the web to that of the non-absorbing reflector. In a manner similar to the calculation of the absorbance spectrum, the corrected or Kubelka-Munk diffuse reflectance spectrum is calculated by taking the square of 1 minus the diffuse reflectance at every wavenumber, divided by two times the diffuse reflectance at that wavenumber. A modified Beer's Law expresses the relationship between the spectrum of signal, $f(r)$ (Kubelka-Munk diffuse reflectance versus wavenumber) as proportional to the concentration ($c_i$) of each component times the turbidity coefficient of that component at each wavenumber ($\tau_i$) times the thickness of the sample.

$$f(r) = (1 - R)^2/2R = \sum_{\text{components, } i} [\tau_i \times (c_i \times 1)]$$

The method described herein refers to absorbances but a method which measures diffuse reflectances is equivalent.

In the fifth step of the method, a baseline absorbance is approximated by constructing straight lines between the absorbance at 2540 wavenumbers, 2676 wavenumbers, 3787 wavenumbers, 4536 wavenumbers, and 4767 wavenumbers. At these wavenumbers none of the components to be measured absorbs radiation, but the silver halide grains in the emulsion scatter light in increasing amounts at higher wavenumbers. Since this light does not pass through the web, it appears as a decreased signal intensity and thus an apparent absorbance that varies with the amount of silver halide, grain size, and morphology, and must be compensated for to determine the web composition. This baseline absorbance spectrum is then subtracted from the sample absorbance spectrum to obtain a corrected sample absorbance spectrum that relates only to the absorbing components of the web. The baseline correction step is illustrated in FIG. 1. For non-photographic webs the baseline points are selected at different wavenumbers but according to the same criteria and the correction process would proceed as described.

In the sixth step of the method, sample integrated absorbance values are obtained, above the baseline described in step 3 (or two other localized baseline points where the band of interest is clearly defined from an underlying broader absorbance), between wavenumbers that have been shown in the calibration step described below to be particularly sensitive to changes in the compositional elements desired. In the case of photographic film these wavenumber ranges include, but are not limited to: 3642-3672 wavenumbers (primarily water in support), 3140-3200 wavenumbers (primarily gel and water in gel), 3090-3108 wavenumbers (gel, support, water in gel), 3012-3020 (support, gel, and water in gel), 3940-4110 (cellulose acetate support), and 4068-4120 (polyethylene terephthalate support). Other wavenumber ranges are used to determine residual cyclohexane in support at 2850-2858 wavenumbers and plasticizer at 3060-3080 wavenumbers.

In the seventh step of the method, the sample integrated absorbance values obtained above are compared to standard support type absorbance values to automatically determine the type of support and hence a future calibration set or set of absorption coefficients to be used in the sixth step. For example, if the integrated area between 4068-4120 wavenumbers is above a certain value, the support has been shown to be polyethylene terephthalate.

Figure 2:
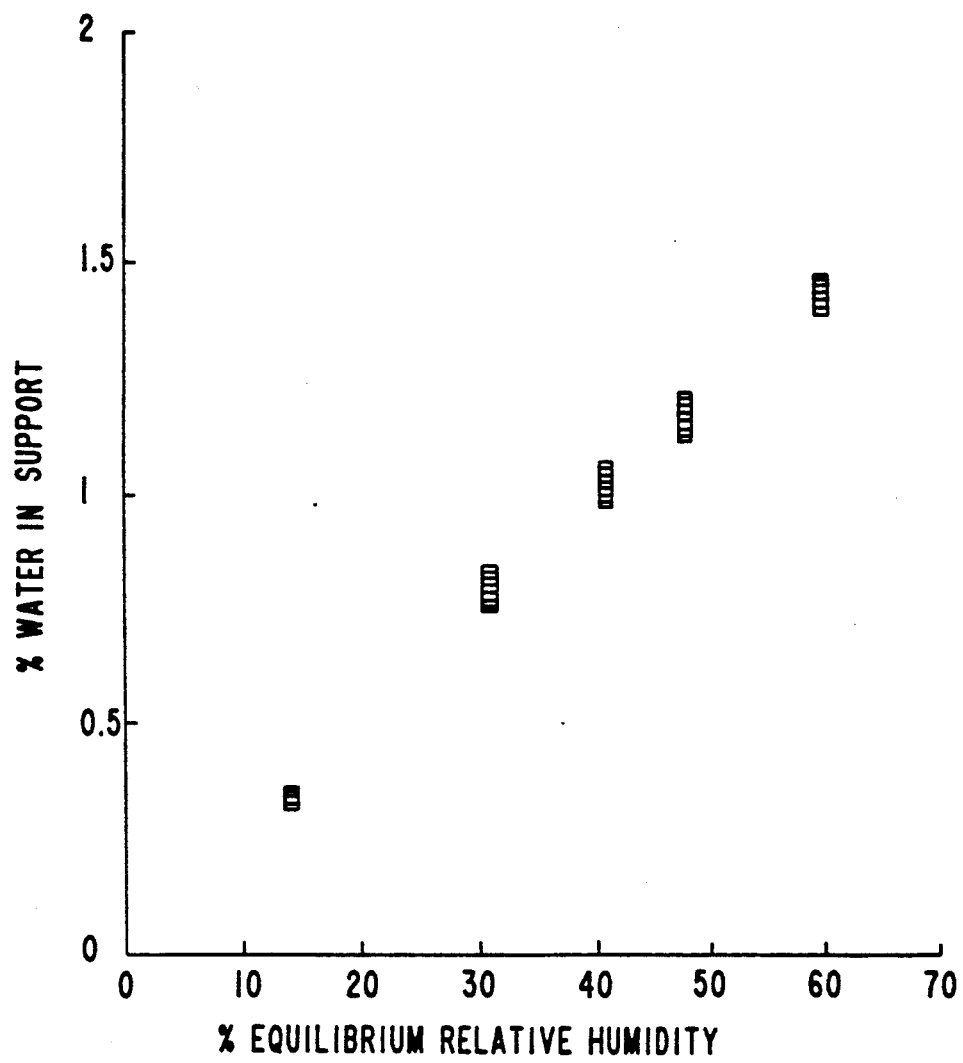
FIG. 2 shows the water content of the support as a function of relative humidity for samples of film A taken over nine production runs.
Figure 3:
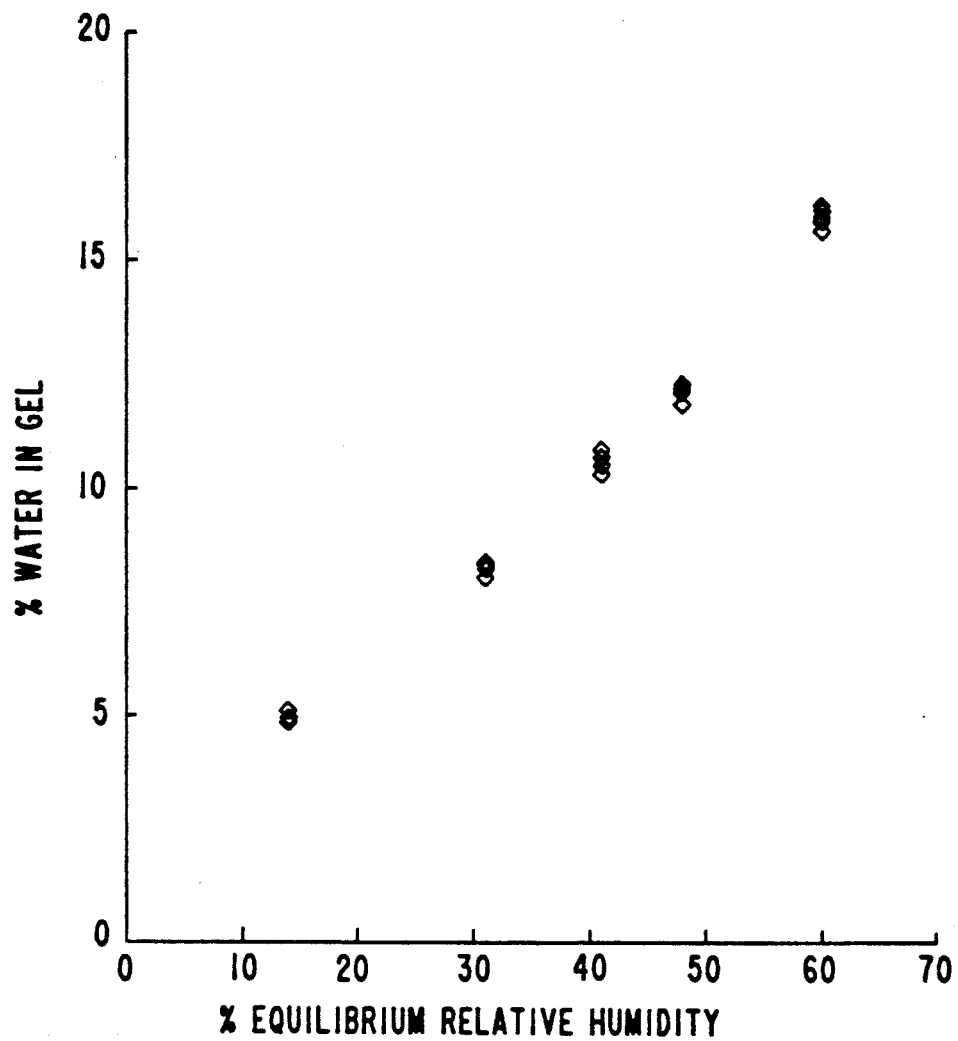
FIG. 3 shows the water content of the gel as a function of relative humidity for samples of film B taken over six production runs.

In the eighth step of the method, the sample integrated absorbance values are combined using Beer's Law and the absorbance coefficients determined in the calibration step described below for each component at each integrated wavenumber range, either sequentially or in parallel to obtain 1) the support thickness in micrometers, 2) the gel laydown in mg/m$^2$, 3) the amount of water in support in mg/m$^2$, and 4) the amount of water in gel in mg/m$^2$. For example, FIGS. 2 and 3 show the water content of support and gel as a function of relative humidity determined for equilibrated samples of film product taken from different coating events.

In one preferred embodiment, the step of determining the coefficients includes the steps of first equilibrating, at various relative humidities, a series of photographic film specimens as well as the supports that these film specimens are coated on, and free standing gel films, each being of known support thickness, support type, and coated gel coverage. Secondly, infrared absorbance spectra in the region 2000 to 6000 wavenumbers were obtained of these films and supports at the various relative humidities. These spectra were then baseline corrected as described above in the third step of the method of the invention and plotted as a function of humidity to show the wavenumbers at which moisture is observed in the support, moisture is observed in the gel, and bands are observed for support and gel.

Figure 4:
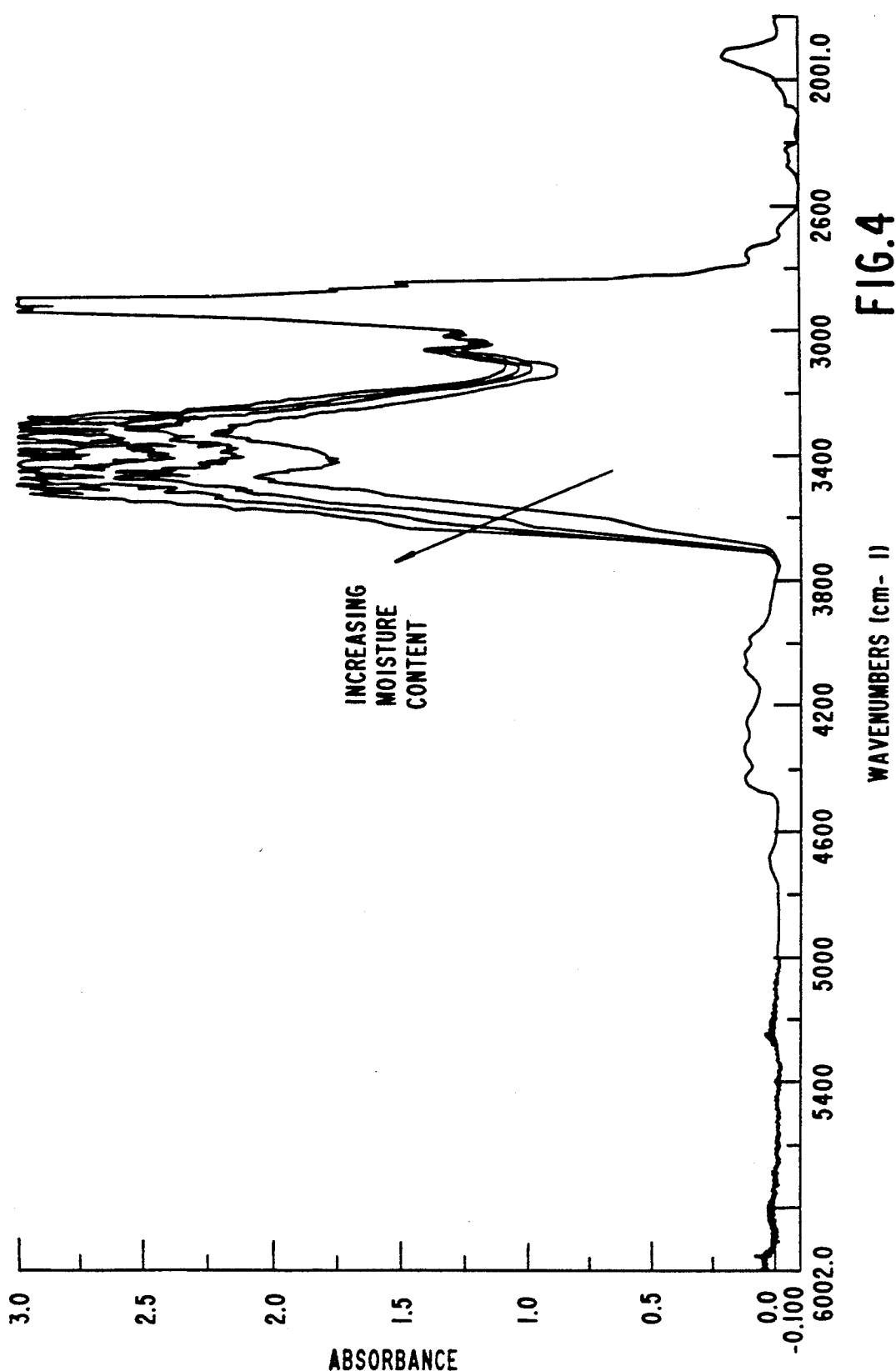
FIG. 4 shows a corrected sample absorbance spectrum for film A at 15, 31, 48, and 60% equilibrium RH.
Figure 5:
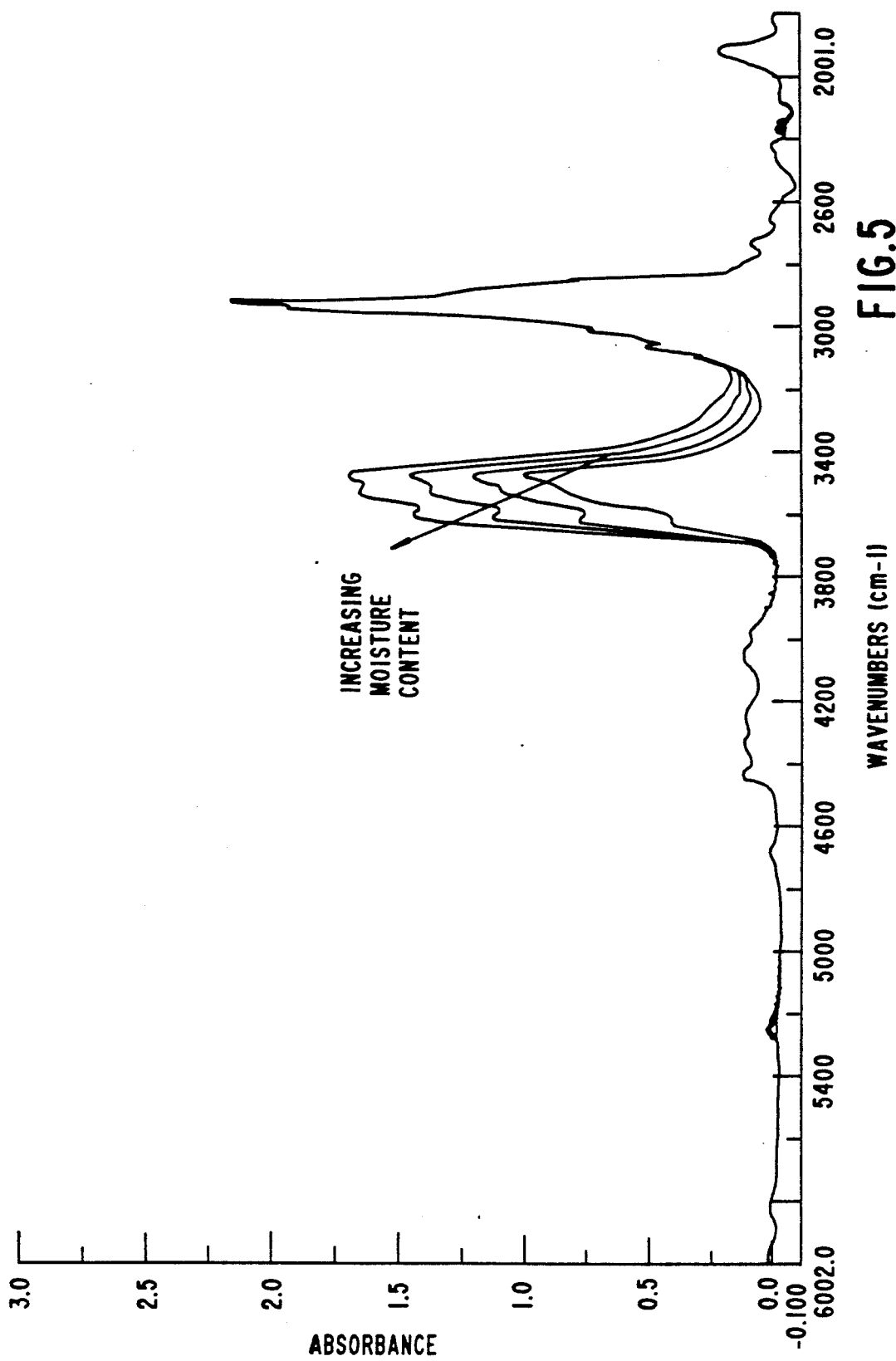
FIG. 5 shows a corrected sample absorbance spectrum for a cellulose acetate support at 15, 31, 48, and 60% equilibrium RH.
Figure 6:
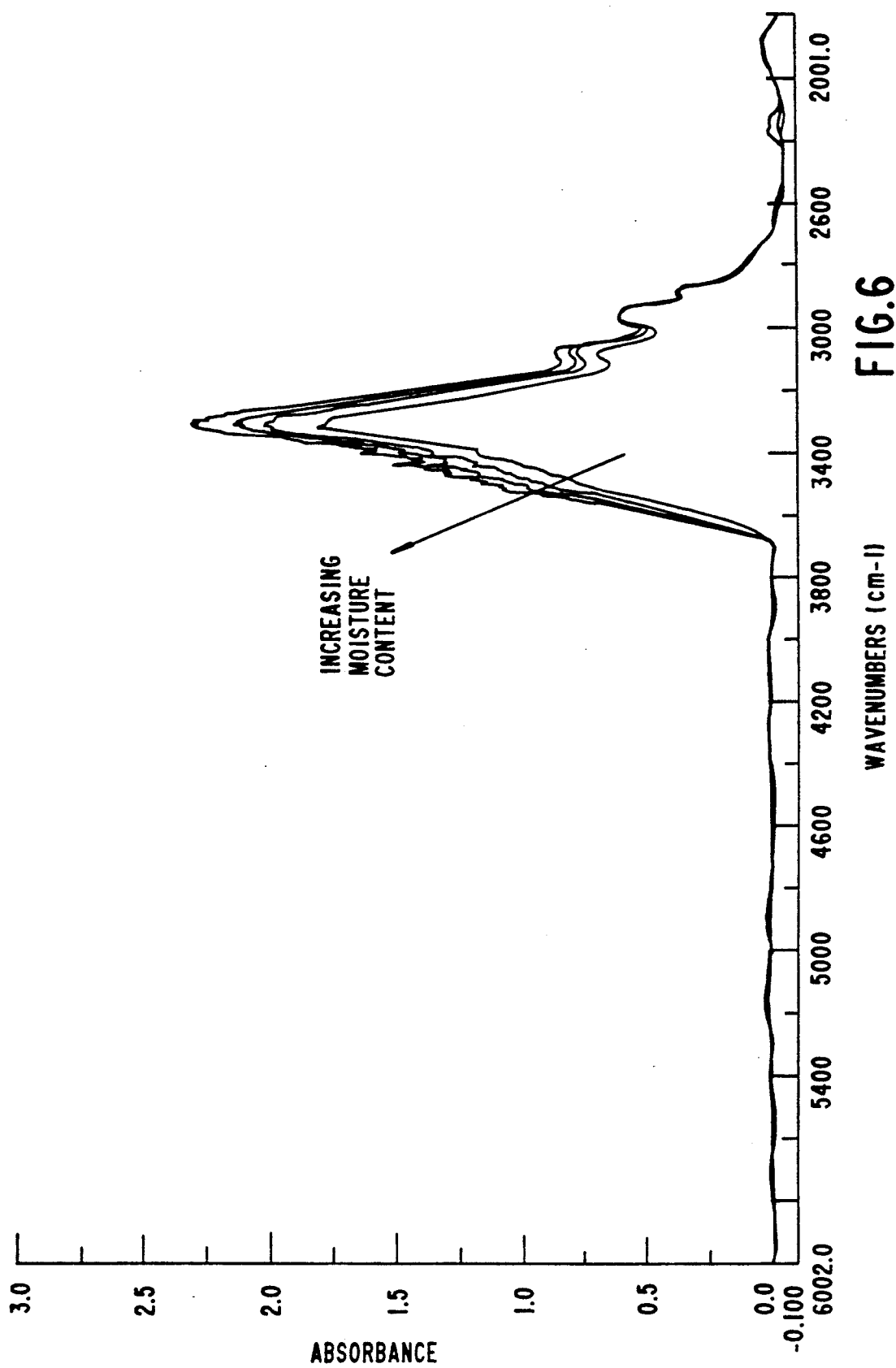
FIG. 6 shows a corrected sample absorbance spectrum for a free standing gelatin film at 15, 31, 48, and 60% equilibrium RH.

FIGS. 4, 5, and 6 show, respectively, the absorbance spectra of a photographic film, an acetate support, and a free standing gelatin film. It is clear from these figures that the spectral features of absorbance versus wavenumber are different for support and for gel and that moisture in support has absorbance between 3200 and 3700 wavenumbers, with a very large absorbance between 3500 and 3700 wavenumbers, while moisture in gel has absorbance between 3000 and 3600 wavenumbers, with a very large absorbance between 3050 wavenumbers and 3300 wavenumbers. It is also clear from these figures that gel itself has a large absorbance spectrum in the region 3000 to 3600 wavenumbers, but different from that of water bound to gel, and that cellulose acetate support has a large absorbance between 2800 and 3100 wavenumbers, although absorbance bands from each of the components are very strongly overlapping so that no component can be said to absorb exclusively at any given wavelength.

An examination of the spectrum of photographic film (FIG. 4) shows that the four just described components act in an additive form in photographic film so that an absorbance at any wavenumber can be considered an additive combination of absorbance due to each component, in agreement with Beer's Law. Finally, FIG. 4 shows that if the absorbance becomes very high, that is, above 3.0 above the baseline, the measurements become very noisy. Therefore, compositional measurements should not be made in those regions of the spectrum. For this reason, the invention does not use wavenumbers between 3200 and 3600 in its preferred embodiment. However, this region could be used advantageously in the analysis of thinner webs. From an analysis of spectra of many photographic films, the regions outlined in step four of the method of the invention are selected as being most useful for compositional analysis.

Finally, integrated absorbance values were obtained in the regions of the spectrum outlined above and combined with measured thicknesses, gel coverages and moisture analysis of the film and support to arrive at a set of calibration factors equivalent to the absorbance coefficients in Beer's Law above that would best fit the measured composition and thicknesses. Stated another way, the Beer's Law equations for individual wavenumber regions represent a series of equations for which, during the calibration step, the absorbance and coverage or thickness of each component are known. Four or more of these equations at any given wavenumber region can be solved to determine the four absorbance coefficients for each component at each wavenumber region. During step six of the method of the invention, for an individual absorbance spectrum one has a set of four or more integrated absorbance values and the attendant absorbance coefficients (four for each absorbance range) that can be combined using Beer's Law to determine the four coverage or thickness values of the sample measured. Statistical methods to accomplish these transformations are abundant in the art and can be either sequential or parallel in time, as for example the partial least squares method.

Unique aspects of this measurement method include, but are not limited to:

1) Differentiation between water bound to hydrophobic or non-hydrogen bonding support and water bound to hydrophilic or hydrogen bonding gelatin because water in the hydrophobic support absorbs in the 3550-3700 wavenumber region (although only the 3640-3670 wavenumber region is used in the preferred embodiment) while water that is hydrogen bonded to gel absorbs in the 3000-3300 wavenumber region (although the 3100-3200 wavenumber region is used for analysis in the preferred embodiment). The wavenumbers indicated are those that are appropriate for analysis; the water absorbances are both much broader than indicated above and do overlap, but support water absorbs at higher wavenumbers than water that is hydrogen bonded to an amide or hydroxyl as in gel.

2) The wavenumber region used in this analysis is in the mid-infrared region where A) the absorbance signals associated with all components are much larger than in the near-infrared region used by commercial web moisture sensors and B) the underlying absorbance background caused by scattering of the infrared by the silver halide particles in photographic emulsions is much less than in the near-infrared. These fundamental phenomena have not been previously combined to provide the advantage of increased signal with less noise. Because of lower background absorbance obtained in the method of the invention this advantage can be achieved.

Furthermore, the mid-infrared region provides a greater separation between wavenumbers that are absorbed by hydrogen-bonded water and wavenumbers that are absorbed by non-hydrogen bonded water than does the near-infrared region. However, the separation between hydrogen-bonded and non-hydrogen bonded water wavenumbers can also be made in the near-infrared region and therefore separate near-infrared measurement of hydrogen-bonded and non-hydrogen bonded water is included in the method of the invention.

3) The method has been developed and is in general used on moving webs using Fourier transform infrared spectrometers (FTIR). FTIR spectrometers provide an advantage over filter-based measurements in that a much larger number of wavelengths are available (several thousand in the preferred embodiment of measurements every 2 wavenumbers) to provide flexibility for multiple film types over multiple support types. Furthermore, the automatic availability of a full spectrum of many discrete wavelengths provides the option for including future analysis for composition elements that may be found to be important or are added in future process changes. For example, it has been possible to measure (in addition to support thickness, gel laydown, water in support, and water in gel) the residual solvent content of underlying support and its plasticizer content.

In addition, the FTIR method provides an advantage over a wavelength or wavenumber scanning full spectrum measurement in that the FTIR obtains information from the entire spectral region during each data collect rather than on a wavelength versus time basis used by a wavelength or wavenumber scanning spectrometer. The advantage is that changes in the film with time are averaged in the FTIR method rather than being observed as spectral features in a scanning method where time correlates with wavelength or wavenumber. Given that disadvantage, however, the method of the invention does not exclude the use of a scanning spectrometer.

Apparently, there has been no other successful application of FTIR alone to the measurement of the composition of a moving web. The FTIR method of the present invention is facilitated because the webs or film products being measured are not patterned, are irregular enough so that fringing is not observed, and contain a diffusely scattering layer. At this time successful measurements have been demonstrated up to 300 m/min on moving film and it is expected that measurements up to 600 m/min and faster are possible.

4) The quantities analyzed are derived from combinations of integrated absorbance values by standard sequential or parallel multi-component methods that assume that the integrated absorbance are linear combinations of coverage or thickness of each component. The analysis does not depend on correlation or spectral fitting as described by Edgar (U.S. Pat. No. 4,885,709).

5) In the preferred embodiment on photographic film, the measurement is made just prior to the film being wound up in a master roll. Moisture content in the wound roll has been shown to be important to photographic performance. This invention provides a unique opportunity to control moisture content in the wound roll and therefore provides a unique advantage for controlling the performance of photographic film. It is in this circumstance of relatively low moisture content that the mid-IR region of the spectrum provides a special advantage.

6) Analysis of selected spectral regions of the obtained transmission spectra allows automatic detection of the support types and automatic selection of a different multi-component analysis of the obtained spectra for each of these unique support types.

7) The method of the invention can be used to measure the amount of water in the support for uncoated webs of support as in support production to provide measurement and control over the amount of moisture in support that will be coated to make photographic film. This control would provide a unique advantage in further controlling the final moisture content in coated photographic film because for some supports it has been demonstrated that the amount of water in the incoming support affects the amount of water in the coated photographic film coated over that support.

EXAMPLES

Example 1

Figure 7:
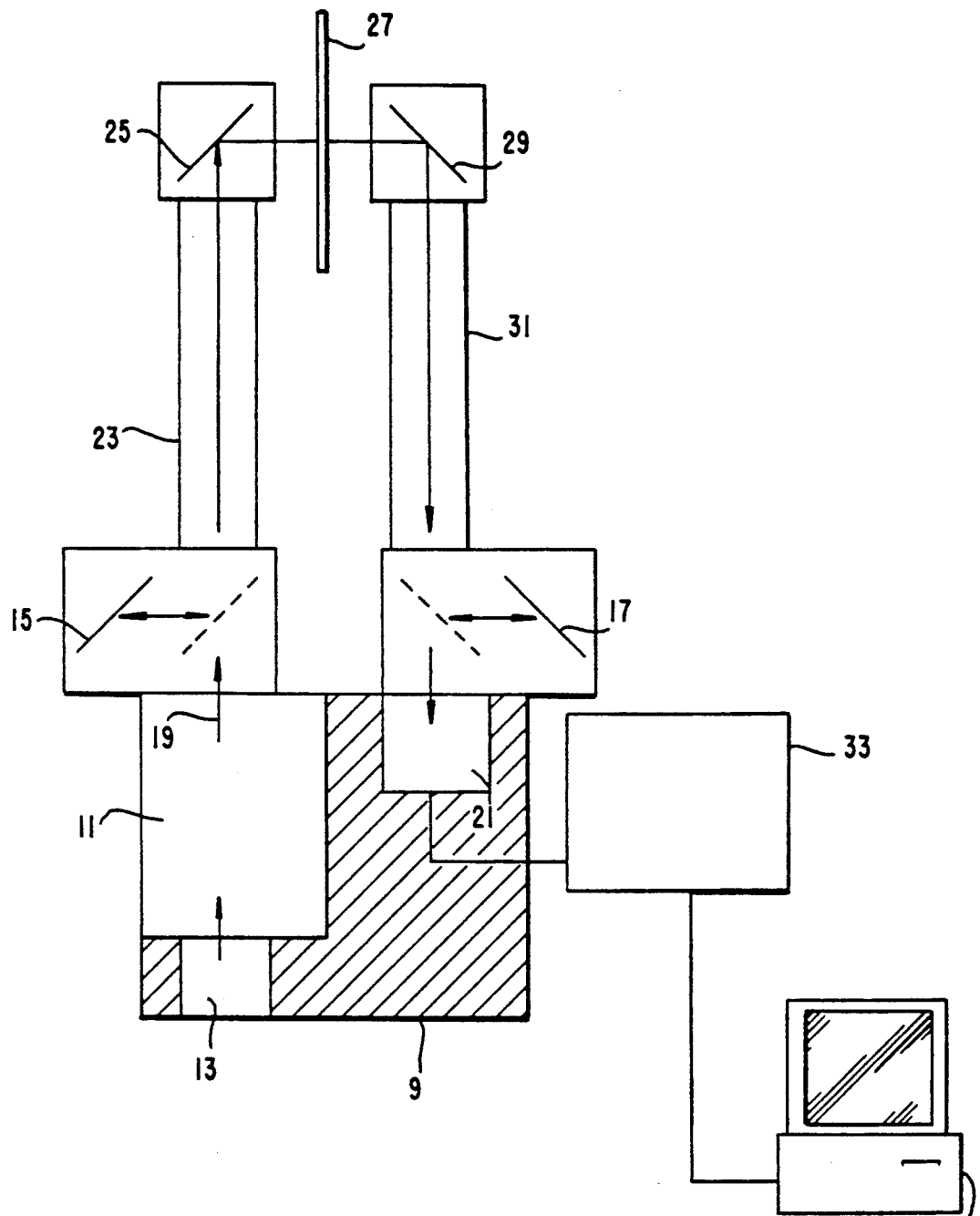
FIG. 7 shows a typical FTIR instrument configuration.

The first example illustrates a typical apparatus used with the invention and a typical calibration step of the method. Referring to FIG. 7, an example of an apparatus used to measure compositional information in multilayer films is an Analect Model PCM 4000 process FTIR spectrometer 9 modified at the output with electrically actuated mirrors 15, 17 and beam transport systems as shown in FIG. 7. With reference to FIG. 7, the source 13 for the Analect Model FX-30 interferometer 11 is a tungsten lamp. At the output of the interferometer 11 is an electrically actuated mirror 15 which, when moved into the path of the collimated output beam 19 reflects the infrared rays through potassium bromide windows and an open path of 3 inches to its mirror image 17 and to a deuterated triglycine sulfate detector 21 to provide the off-web reference path. When the movable mirror 15 is moved out of the infrared path, the collimated infrared rays 19 from the interferometer 11 are projected through a 15 inch segment of closed 2 inch diameter tubing 23 to a fixed mirror 25, potassium bromide windows, and an open path of 3 inches containing the multilayer web 27 to be measured, and then returned to the same detector 21 with an identical mirror 29 and tubing 31. Interferograms of all infrared rays between 800 wavenumbers and 6000 wavenumbers (the range is limited by the detector) in either the background or web path are averaged for 30 seconds to two minutes, depending on the application, in the Analect DCM control computer 33 and then sent to the data analysis computer 35, an Analect 16 MHz 80386SX AT compatible, for analysis according to the method outlined in this application. In a typical calibration step, 98 samples of production runs of various photographic film products, supports and gelatin films representing variations in support thickness of 0 to 8.5 mils and including four different support types, and gel coverages between 0 and 27,000 mg/m$^2$, were equilibrated sequentially at five different relative humidities (RH) between 15% and 65% RH at 70° F. At each relative humidity, the apparatus defined above was used to measure a reference background single beam interferogram averaged over 2 minutes. Interferograms of each static sample were measured in duplicate 1 minute averages in a random sequence. The background and sample interferograms were transformed by Fourier methods to single beam spectra; these were divided to obtain the sample transmission spectra; and finally these were converted to sample absorbance spectra between 2000 wavenumbers and 6000 wavenumbers. Baseline spectra were obtained by drawing straight lines between the absorbances at 2540, 2676, 4536, and 4767 wavenumbers and these baseline spectra were subtracted from the sample absorbance spectra to compensate for light scattering by the samples. Examples of such baseline corrected spectra for film A are shown in FIG. 4.

Integrated absorbance areas were calculated from these corrected spectra between 4068–4120 wavenumbers, 3940–4110 wavenumbers, 3642–3672 wavenumbers, 3140–3200 wavenumbers, 3090–3108 wavenumbers, and 3012–3020 wavenumbers. For each of the four different support types, these areas, along with known measurements of support thickness, gel coverage, gel moisture from measured isotherms, and support moisture from measured isotherms, were analyzed with the multiple linear regression statistics module of Systat, a PC-based statistics program, to obtain average coefficients relating the measured absorbances to the measured quantities. These coefficients are then used to predict the measured quantities of each sample from the integrated areas. Because the actual quantities of moisture in gel or support are directly related to the thickness of gel or support at any relative humidity, comparisons between samples were made on the basis of the percentage of moisture in support or gel (mass/area of moisture $\times$ 100/mass/area of support or gel). Examples of these percentage moisture measurements versus relative humidity are shown in FIGS. 2 and 3 for samples of different lots of two photographic film types.

Example 2

This example illustrates a comparison with commercial near-infrared moisture measurements. Four film samples were selected as examples of multilayer photographic film on cellulose acetate support having different amounts of silver halide particles. The apparatus outlined in Example #1 was used along with the method outlined therein to obtain the sample absorbance spectra of these stationary films at six different relative humidities at 70° F., corrected for scattering. The ratios of the integrated intensity at 3642–3672 wavenumbers to that at 3012–3020 wavenumbers was fit to a linear model versus the relative humidity of the measurement to obtain an average calibration coefficient of ratio versus relative humidity. That average coefficient was multiplied by the individual ratios to obtain a plot of predicted versus actual relative humidity shown as the squares in FIG. 8.

Figure 8:
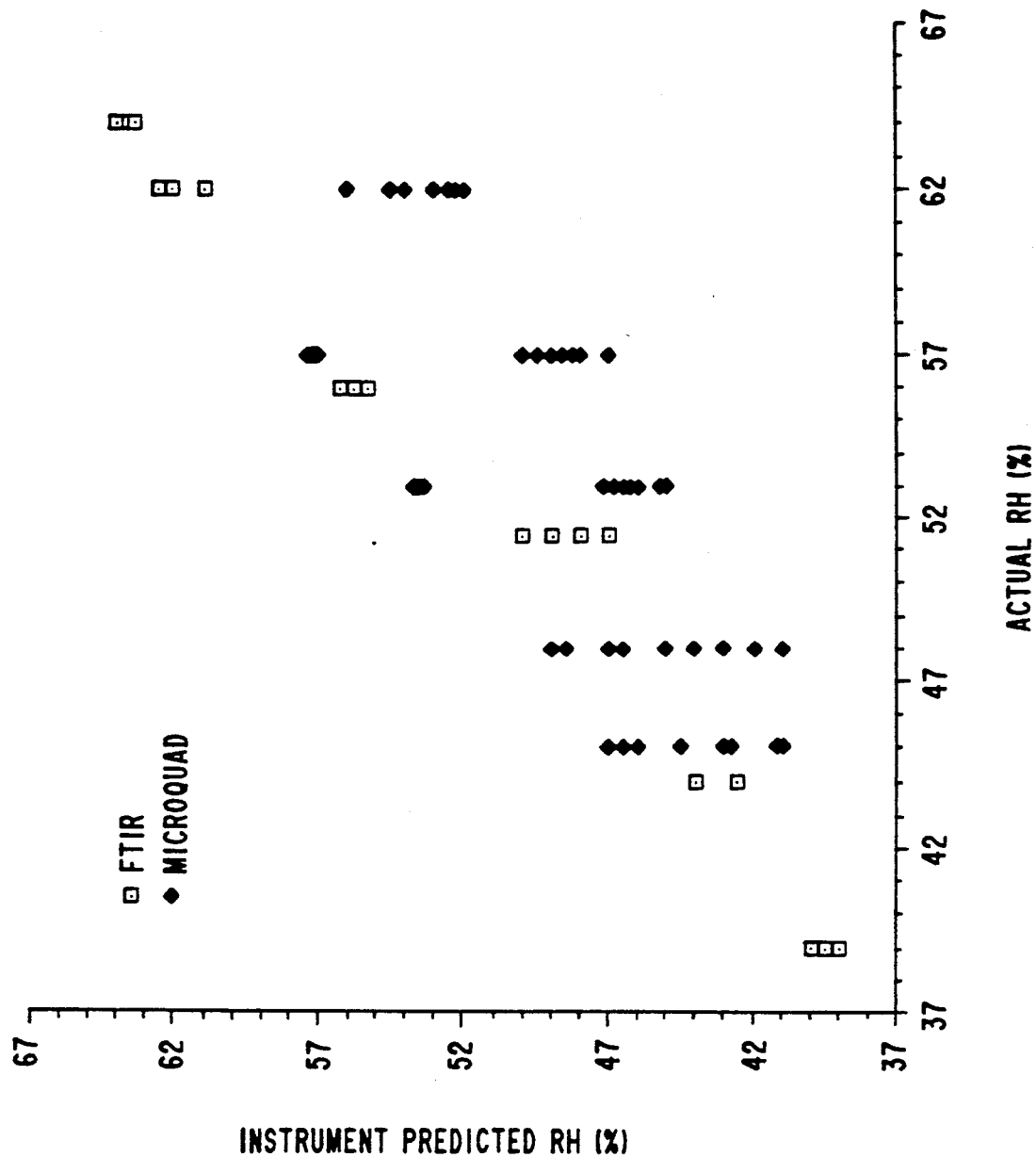
FIG. 8 shows a comparison of moisture measurements on four different film types between the method of the present invention and a conventional method.
Figure 9C:
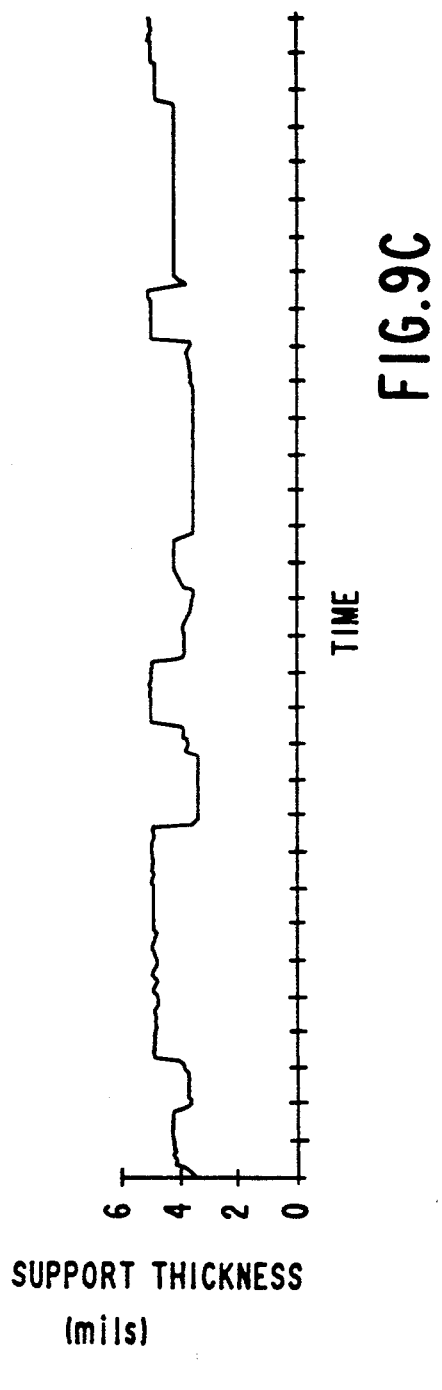
Figure 9D:
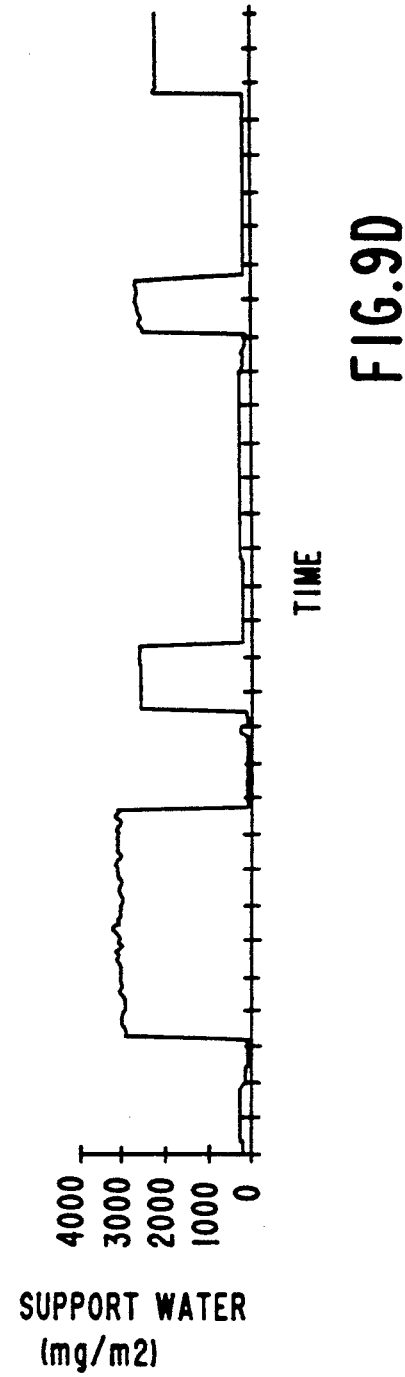

A commercial filter near-infrared moisture sensor, the Micro-Quad 8000 from Moisture Systems Corp., was used to measure the same samples using a previously determined calibration method provided by the manufacturer. The results of that measurement are also shown in FIG. 8 by the diamond shaped points. It is clear that the mid-infrared FTIR method is far more precise than this commercially available method. For a given actual relative humidity, represented by points on the x-axis, the relative humidities predicted by the FTIR method are consistently closer to the actual relative humidities than are those predicted by the Micro-Quad method.

Example 3

This example illustrates an on-line measurement of a moving web. In this example the apparatus outlined in Example #1 was installed at a point approximately 6 feet from the point at which film is wound into rolls at the end of a coating machine used to manufacture experimental photographic films. During manufacturing operation the reference background is a 1 minute average obtained every 30 minutes. Sample measurements on the moving web are sequential 30 second averages. These are processed in the data analysis computer using the method outlined in Example 1 and the coefficients determined in the calibration step outlined there, to obtain measurements of support thickness, gel coverage, moisture (water) in support and moisture (water) in gel. In FIGS. 9A–D, those outputs are plotted versus time for a typical experimental coating event. The experiment consisted of four gel coatings on cellulose acetate support (portions of the figure where gel coverage is not zero), each with different drying conditions that produce different final moisture contents. The first coating was dried less harshly and the last more harshly than the middle two coatings which have identical drying conditions. Between these coating events the apparatus measured compositional information on uncoated polyethylene terephthalate leader. This example shows the excellence of the measurements of compositional information as well as the excellent lack of noise in sequential 30 second measurements where each mark on the time axis represents 5 minutes.

It will be appreciated that the present invention can be embodied in other specific forms without departing from the spirit or essential characteristics thereof. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for determining compositional information of a multilayer web comprising the steps of:
   a) determining at least one set of coefficients from specimens of multilayer webs having known compositional information, each set of coefficients including a coefficient for each item of compositional information to be determined, each set of coefficients being calculated for a selected wavenumber range, a number of selected wavenumber ranges being at least equal to the number of items of compositional information to be determined;
   b) generating a broad spectrum of infrared rays;
   c) projecting said broad spectrum of infrared rays through open air off the sample web;
   d) detecting said broad spectrum projected off the sample web to obtain a single beam background spectrum;
   e) projecting said broad spectrum of infrared rays onto a sample web;
   f) detecting said broad spectrum projected onto the sample web to obtain a sample single beam spectrum;
   g) calculating a sample spectrum from the single beam background spectrum and the sample single beam spectrum;
   h) obtaining a corrected sample spectrum by subtracting a baseline spectrum from the sample spectrum;
   i) integrating the corrected sample spectrum, the integration performed for each selected wavenumber range used in calculating the coefficients in step a), thereby defining sample integrated values for each selected wavenumber range;

j) comparing the sample integrated values to standard support type values to determine a type of support in the multilayer web and a corresponding set of coefficients from step a) to be used in step k); and k) combining the sample integrated values with the set of coefficients to solve at least one equation for the values of the items of compositional information to be determined.

2. The method of claim 1 wherein the spectra are absorbance spectra and the at least one equation is a Beer's Law equation.

3. The method of claim 1 wherein the spectra are Kubelka-Munk diffuse reflectance spectra and the at least one equation is a modified Beer's Law equation.

4. The method of claim 1 wherein the determining step includes determining coefficients from specimens of multilayer webs having hydrophobic and hydrophilic layers.

5. The method of claim 4 wherein the items of compositional information to be determined by solving the at least one equation include support thickness, gel laydown, the amount of water in the support, and the amount of water in the gel.

6. The method of claim 1 wherein the determining step includes determining coefficients from specimens of multilayer webs that are light scattering.

7. The method of claim 1 wherein the step of projecting said broad spectrum of infrared rays through open air off the web is performed while the multilayer web is moving at process speed, the broad spectrum of infrared rays being projected in an area immediately adjacent to the moving web, whereby the composition of the open air through which the broad spectrum of infrared rays are projected is obtained is substantially equal to the composition of the air over the moving web.

8. The method of claim 1 wherein the step of obtaining a corrected sample spectrum includes the step of:

constructing the baseline spectrum by constructing straight lines between wavenumbers at which components to be measured are not absorptive of radiation beyond that lost to infrared scattering.

9. The method of claim 8 wherein the straight lines are constructed between the wavenumbers of about 2540, 2676, 3787, 4536, and 4767.

10. The method of claim 1 wherein the step of determining at least one set of coefficients includes the steps of:

equilibrating, at a plurality of relative humidities, a series of specimen webs, supports for each of the specimen webs, and free standing gelatin films for each of the specimen webs, each of the specimen webs, supports, and gelatin films being of known thickness, type, and coated gel coverage;

projecting a broad spectrum of infrared rays onto each of the specimen webs, supports, and gelatin films at each of the relative humidities to obtain specimen single beam spectra;

projecting a broad spectrum of infrared rays through open air off each of the specimen webs, supports, and gelatin films at each of the relative humidities to obtain single beam background spectra;

calculating specimen spectra from the specimen single beam spectra and the single beam background spectra;

obtaining corrected spectra of each of the specimen webs, supports, and gelatin films by subtracting baseline spectra from the specimen spectra;

plotting the corrected spectra for each of the various relative humidities;

selecting wavenumber ranges from the plotted corrected spectra that are sensitive to the items of compositional information to be determined;

integrating the corrected spectra over the selected wavenumber ranges, thereby defining specimen integrated values for each selected wavenumber range; and combining the specimen integrated values with the known thicknesses, types, and coated gel coverages to solve a set of equations for a set of coefficients for each selected wavenumber range.

11. The method of claim 10 wherein the step of selecting wavenumber ranges includes selecting wavenumber ranges from portions of the spectra where corrected values are no more than 3.5 units above the baseline.

12. The method of claim 11 wherein the step of selecting wavenumber ranges includes selecting at least one of the wavenumber ranges of about 3642–3672, 3140–3200, 3090–3108, 3012–3020, 3940–4110, 4068–4120, 2850–2858, and 3060–3080.

13. The method of claim 1 wherein the step of projecting said broad spectrum of infrared rays onto a sample web includes projecting the broad spectrum of infrared rays at times when the multilayer web is moving at speeds up to 600 m/min.

* * * * *

UNITED STATES PATENT AND TRADEMARK OFFICE
CERTIFICATE OF CORRECTION

PATENT NO. : 5,250,811
DATED : October 5, 1993
INVENTOR(S) : Lippert, et. al.

It is certified that error appears in the above-indentified patent and that said Letters Patent is hereby corrected as shown below:

Title page, item [75] inventor: should read--Joseph L. Lippert--.

Column 5, line 39, after "web". insert new paragraph.

Column 7, line 4, before "water" insert --and--.

Column 10, line 54, after "appliacation." insert new paragraph--.

Signed and Sealed this

Ninth Day of August, 1994

Attest:

BRUCE LEHMAN

*Attesting Officer*     *Commissioner of Patents and Trademarks*